United States Patent [19]
Yamamura et al.

[11] Patent Number: 5,382,490
[45] Date of Patent: Jan. 17, 1995

[54] ELECTROPHOTOGRAPHIC TONER

[75] Inventors: Shigeo Yamamura, Omiya; Junko Yamamoto, Kawaguchi; Tadayuki Kiyoyanagi, Urawa; Masaharu Nomura, Hasuda, all of Japan

[73] Assignee: Nippon Kayaku Kabushiki Kaisha, Tokyo, Japan

[21] Appl. No.: 931,705

[22] Filed: Aug. 18, 1992

[30] Foreign Application Priority Data

Aug. 30, 1991 [JP] Japan .................................. 3-244329
Jun. 30, 1992 [JP] Japan .................................. 4-194558

[51] Int. Cl.$^6$ .............................................. G03G 9/00
[52] U.S. Cl. ..................................... 430/110; 430/109
[58] Field of Search ................................. 430/110, 109

[56] References Cited

U.S. PATENT DOCUMENTS

| | | | |
|---|---|---|---|
| 1,926,874 | 9/1933 | Klarmann et al. | 260/64 |
| 4,147,645 | 4/1979 | Lu | 252/62.1 |
| 4,480,021 | 10/1984 | Lu et al. | 430/106.6 |
| 5,017,728 | 5/1991 | McKinnie et al. | 568/726 |

FOREIGN PATENT DOCUMENTS

| | | |
|---|---|---|
| 0380159 | 1/1990 | European Pat. Off. . |
| 61-3149 | 1/1986 | Japan . |
| 63-38958 | 2/1988 | Japan . |
| 2216125 | 4/1989 | United Kingdom . |

*Primary Examiner*—S. Rosasco
*Attorney, Agent, or Firm*—Nields & Lemack

[57] ABSTRACT

An electrophotographic toner containing a specific compound as the charge control agent is described. The electrophotographic toner according to the present invention have a sharper distribution of charge and better moisture resistance and charge durability than those of a toner wherein a conventional charge control agent is used. Therefore it can provide an image having a very high gradation and has a very high capability of repeatedly forming an image. Since the charge control agent, as such, is essentially colorless, a colorant can freely be selected according to a hue required of a color toner and the toner is not detrimental to the hue inherent in a dye and a pigment. The charge control agent is highly safe to environment.

6 Claims, 2 Drawing Sheets

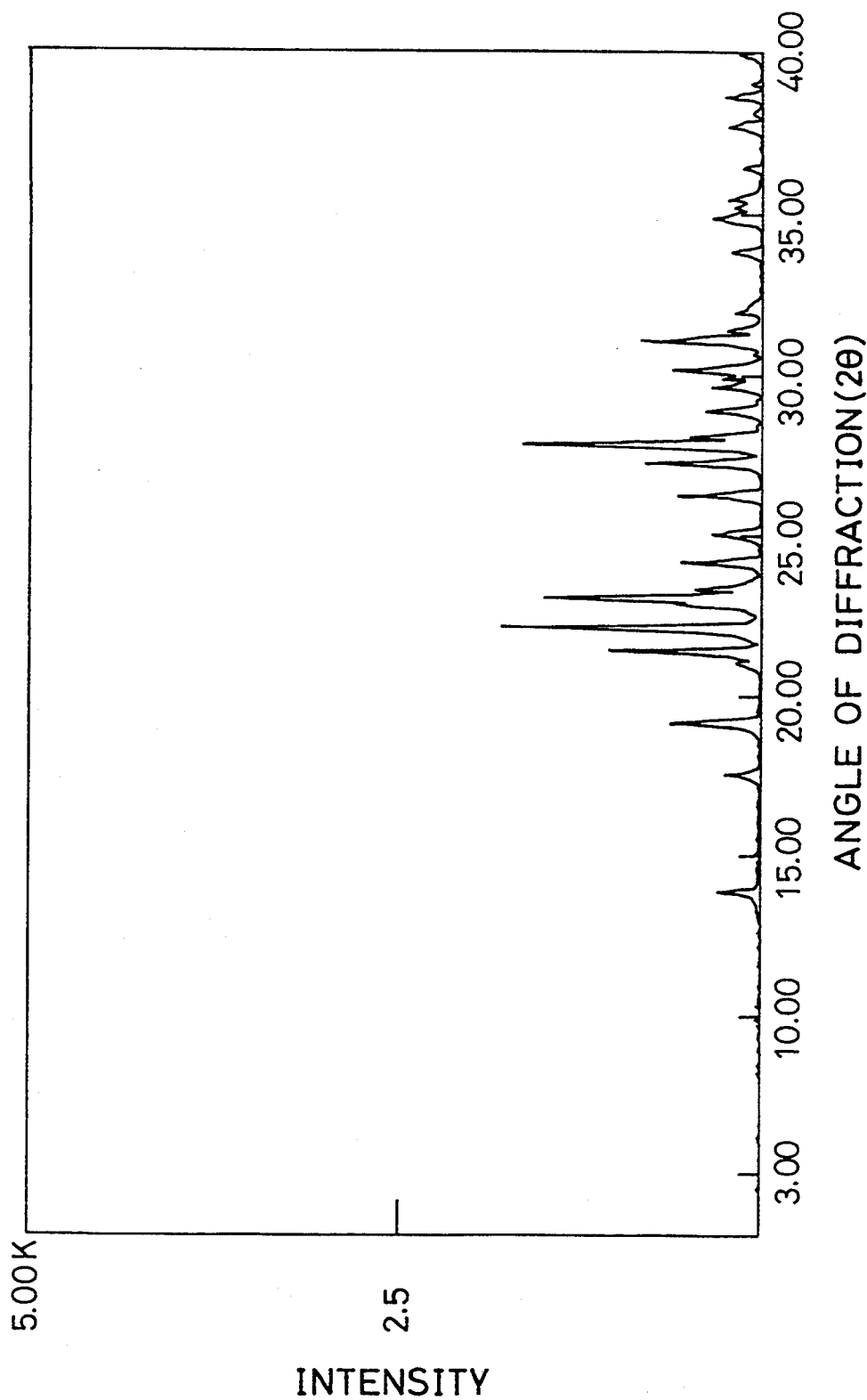

ELECTROPHOTOGRAPHIC TONER

BACKGROUND OF THE INVENTION

The present invention relates to a toner used for developing an electrostatic latent image in an electrophotography, an electrostatic recording, etc.

An imaging process wherein use is made of static electricity, such as electrostatic recording or electrostatic photography, comprises the step of forming an electrostatic latent image and the step of visualizing the electrostatic latent image. The electrostatic latent image is formed by light signal on a photosensitive material prepared by coating a base material such as aluminum and paper with a photoconductive material such as phthalocyanine pigment, selenium, cadmium sulfide and amorphous silicon. The electrostatic latent image thus formed is visualized by subjecting colored fine particles called toner having a particle diameter regulated to 5 to 50 μm to contact chargeability with a charge carrier such as iron powder and ferrite powder (two-component development) or to direct chargeability (one-component development) and then allowing the charged toner to act on the electrostatic latent image. It is necessary to impart a charge corresponding to the polarity of the electrostatic latent image formed on the photoconductive material, that is, either a positive charge or a negative charge, to the toner.

The colored fine particle called toner generally comprises a binder resin as the main component as well as a colorant and charge control agent. Among them, the charge control agent is particularly important component which controls the retainment of the electric charge generated by contact chargeability with a carrier and charging properties of the toner. Although an electric charge can be imparted to the toner through the utilization of a chargeability property of colorant and the binder resin per se without using any charge control agent, only extremely poor image quality can be obtained due to occurrence of fogging phenomena derived from poor chargeability. Quality characteristics required of the toner other than chargeability include excellent stability, fluidity and fixing property. These quality characteristics are greatly affected by the charge control agent used for the toner.

Examples of the conventional charge control agent added to the toner include (1) colored negative charge control agents such as 2:1 metallic complex salt dyes (Japanese Patent Publication (KOKOKU) Nos. 26478/1970 and 20153/1966) and phthalocyanine pigments (Japanese Patent Application Laid-Open (KOKAI) No. 45931/1977), and colorless negative charge control agents such as metal complexes of aromatic dicarboxylic acids (Japanese Patent Publication (KOKOKU) No. 7384/1984), metal complexes of salicylic acid (Japanese Patent Application Laid-Open (KOKAI) No. 104940/1982), or those described in Japanese Patent Application Laid-Open (KOKAI) No. 3149/1986; and (2) positive charge control agents such as nigrosine dyes, triphenylmethane dyes, various quaternary ammonium salts (Bulletin of the Institute of Electrostatics Japan, vol. 4, No. 3, P. 114 (1980)) and organotin compounds such as dibutyltin oxide (Japanese Patent Publication (KOKOKU) No. 29704/1982). The toners containing these compounds as the charge control agent, however, do not sufficiently satisfy the quality characteristics required for the toner, such as chargeability and charge durability (an ability to maintain a charge for a long time).

For example, although the amount of chargeability of the toner containing a 2:1 metallic complex salt dye known as the negative charge control agent is on a fair level, this dye is disadvantageously poor in the dispersibility in a binder resin on the whole. For this reason, the dye is not homogeneously dispersed in the binder resin, and the distribution of charge extremely lacks in sharpness. The resultant image has a low gradation and is poor in the image forming capability.

Further, the 2:1 metallic complex salt dye is disadvantageous because it cannot be used but for a toner having a shade of color limited to black or blackish hue. The use of this dye for a color toner is detrimental to the brightness of the colorant.

Examples of the nearly colorless negative charge control agent include a metal complex of an aromatic dicarboxylic acid (Japanese Patent Publication (KOKOKU) No. 7384/1984). This charge control agent, however, is disadvantageous in that it cannot become completely colorless and the dispersibility is poor. A metal complex of salicylic acid is a colorless charge control agent having relatively good chargeability (Japanese Patent Application Laid-Open (KOKAI) No. 104940/1982), but causes safety problems owing to its inclusion of a heavy metal. Examples of the colorless negative charge control agent containing no heavy metal include compounds disclosed in Japanese Patent Application Laid-Open (KOKAI) Nos. 3149/1986 and 38958/1988. These compounds, however, are disadvantageous in that it is difficult to produce toners having a good stability because the melting points of the compounds are lower than the processing temperature (180°–260° C.) and various troubles may occur during the toner processing, and that the rise of the charge is slow.

The nigrosine dyes and triphenylmethane dyes known as positive charge control agents as well are colored and therefore can be used only for a toner having a color limited to black or blackish color. They are also poor in the charge durability in continuous copying. The quaternary ammonium salt, when incorporated in a toner, has a poor charge durability attributable to its insufficient moisture resistance and therefore cannot provide an image having a good quality in repeated use.

Japanese Patent Publication (KOKOKU) No. 16109/1992 describes that bisphenol compounds act as good charge control agents in toner. However, these compounds do not exhibit sufficient effect as charge control agents owing to their relatively large particle size, i.e., 10–15 μm.

Thus, the conventional charge control agents do not sufficiently satisfy the quality characteristics requirements for the toner.

SUMMARY OF THE INVENTION

An object of the present invention is to provide an electrophotographic toner containing a colorless positive or negative charge control agent containing no heavy metal and having an excellency in the rise of the charge, excellent chargeability and charge durability, and a good dispersibility during the production of the toner. The charge control agent contained in the above electrophotographic toner is at least one compound represented by the following formula (1):

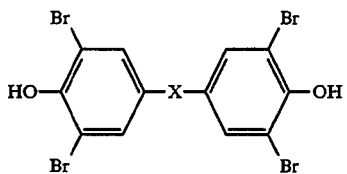

wherein X represents —$SO_2$— or —$C(CH_3)_2$—.

The present charge control agent has good dispersibility during the production of toner and improves chargeability properties. Thus, the electrophotographic toner according to the present invention have a sharper distribution of charge and better moisture resistance and charge durability than those of a toner wherein a conventional charge control agent is used. Therefore it can provide an image having a very high gradation and has a very high capability of repeatedly forming an image. Since the charge control agent, as such, is essentially colorless, a colorant can freely be selected according to a hue required of a color toner and the toner is not detrimental to the hue inherent in a dye and a pigment. The charge control agent is also less harmful to environment.

DETAILED DESCRIPTION OF THE INVENTION

More precisely, the present invention provides:
1) An electrophotographic toner containing at least one compound represented by the following formula (1) which acts as a charge control agent.

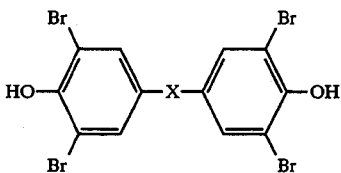

wherein X represents —$SO_2$— or —$C(CH_3)_2$—.

2) An electrophotographic toner containing the compound represented by the formula (1) wherein the particle size of the compound is 5 μm or less.
3) A process for preparing the compound represented by the formula (1) comprising dissolving the compound represented by the formula (1) in an alkaline solution and then precipitating its crystals by using an acid.

The compound represented by the above formula (1) wherein X represents —$SO_2$— is preferred.

Since the charge control agent of the formula (1) for the toner according to the present invention has a good compatibility with a binder resin, and a toner containing this compound has a high specific chargeability and charge durability and therefore can stably provide a clear image in the image formation through electrostatic recording even after storage for a long period of time. Since the compound of the formula (1) is colorless, it is easy to prepare any colored toners and black toner starting with the compound. In addition, this compound does not contain any heavy metal which may cause safety problems in the environments. Furthermore, the toner can be produced steadily owing to the lack of polymerization inhibitory action which may be observed in the production of toner via suspension polymerization or emulsion polymerization using metal-containing charge control agent.

The compounds represented by the above formula (1) can be prepared by, for example, brominating 4,4'-dihydroxydiphenylsulfone or 4,4'-dihydroxydiphenyl-2,2-propane with a brominating agent such as bromine or hydrobromic acid in alcoholic or sulfuric acid solvent preferably at 0° to 80° C. according to a conventional process. The brominating agent is used in an amount of 4 to 8 molar equivalents to the compounds of the formula (1). Optionally, the compounds may be prepared as a form of fine particles according to the following method: A compound of the formula (1) is added to an alkaline solution and completely dissolved thereinto under stirring. Crystals are precipitated by neutralizing the resulting aqueous solution with adding an acidic aqueous solution or by pouring the resulting aqueous solution to an acidic aqueous solution, thereby fine particles of the compound of the formula (1) being obtained. The temperature for dissolving the compound of the formula (1) and for precipitating crystals with an acid is in the range of 0° C. to 90° C., preferably 15° C. to 30° C. The alkaline agent to be used may be an alkali metal compound or alkaline earth compound, preferably sodium hydroxide, sodium carbonate, potassium hydroxide, or potassium carbonate. The amount of the alkaline agent may be usually 1 to 3 molar equivalents to the compound of the formula (1) and the concentration of the alkaline solution may be usually 5 to 30% by weight. The neutralization (precipitation of crystals) can be conducted by adding a mineral acid or an organic acid, preferably sulfuric acid, hydrochloric acid, acetic acid, or the like. The acid may be added in an amount so as to become the pH of the alkaline solution containing the compound of the formula (1) to 2 to 6, preferably 4 to 6. The concentration of the acid used is in the range of 3 to 95% by weight, preferably 5 to 20% by weight.

The crystals obtained in the above process is in a form of uniform fine particles having a diameter of 5 μm or less, preferably 1 to 3 μm.

A toner containing the compound represented by the above-described formula (1) can be prepared by a process which comprises kneading a mixture of a compound of the formula (1), a colorant and a binder resin in an apparatus capable of conducting heat mixing, such as a heat kneader and a twin roll, in such a state that the binder resin is in a molten state, cooling the kneaded product for solidification and pulverizing the solid into particles having a diameter of 3 to 20 μm by means of a pulverizer such as a jet mill and a ball mill. A process which comprises dissolving a colorant, a binder and a compound represented by the formula (1) in a solvent such as acetone and ethyl acetate, stirring the resultant solution, pouring the solution into water for re-precipitation, subjecting the precipitate to filtration and drying, pulverizing the dried solid into particles having a diameter of 3 to 20 μm by means of a pulverizer such as a ball mill, is also applicable. An alternative process comprises dispersing homogeneously into water a compound of the formula (1), a colorant and monomer(s) of a binder resin, polymerizing the monomer(s) in a form of fine particles under stirring to produce precipitates, converting the precipitates into a fine powder by successive filtration, washing with water and drying, and classifying the powder to obtain an aimed product having a particle diameter of 3 to 20 μm. Furthermore, a core material on soft particles (core particles) containing a low-melting resin for pressure fixing, a colorant, and magnetic substance, which is covered with a hard outer shell which provides protection and charge control functions can be used as microcapsule toner. In addition, the compound of the formula (1) alone or in combination with other additives such as colloidal silica can be fixed, by means of mechanochemical procedure or the like, on the surface of the colored fine particles containing no charge controlling material prepared according to one of the above mentioned processes.

In general, the proportion of the binder resin in toner is 99 to 65% (by weight; the same shall apply hereinafter), preferably 98 to 85%, the proportion of the colorant is 1.0 to 15%, preferably 1.5 to 10%, and the proportion of the charge control agent is 0.1 to 30%, preferably 0.5 to 5%. Other charge control agents can be used in combination with the agents of the present invention.

Examples of the colorant useable in the electrophotographic toner of the present invention include colorants known in the art, for example, inorganic pigments such as carbon black, ultramarine, iron black, active carbon, copper oxide, manganese dioxide, chrome yellow, zinc yellow, cadmium yellow, yellow iron oxide, Mineral Fast Yellow, nickel titanium yellow, red-colored chrome yellow, molibdenum orange, red iron oxide, cadmium red, manganese purple, titanium oxide, zinc sulfide, chrome green, chromium oxide, and antimony white; organic pigments such as CI. (abbreviation for Color Index; the same shall apply hereinafter) Pigment Yellow 1, CI. Pigment Red 9, CI. Pigment Blue 15, Aniline Black, Naphthol Yellow S, Benzidine Yellow GR, Quinoline Yellow Lake, Anthrapyrimidine Yellow, Hansa Yellow G, Permanent Yellow NCG, Pyrazolone Orange, Indanethrene Brilliant Orange GK, Pyrazolone Red, Brilliant Carmine 6B, Rhodamine Lake B, Quinacridone, Alizarine Lake, Thioindigo Red, Thioindigo Maroon, Brilliant Carmine 3B, Methyl Violet Lake, Dioxadine Violet, Aniline Blue, Non-metallic Phthalocyanine Blue, Phthalocyanine Blue, Fast Sky Blue, Indanthrene Blue BC, Phthalocyanine Green, Malachite Green Lake, and Final Yellow Green G; and oil-soluble dyes such as CI. Solvent Yellow 93, CI. Solvent Red 146, CI. Solvent Blue 35, CI. Disperse Yellow 42, CI. Disperse Red 59, CI. Disperse Blue 81, CI. Solvent Red 49, CI. Solvent Red 52, CI. Solvent Red 109, CI. Basic Red 12, CI. Basic Red 1, CI. Direct Red 1, CI. Acid Red 1, CI. Basic Red 1, CI. Direct Red 4, CI. Mordant Red 30, CI. Direct Blue 2, CI. Acid Blue 9, CI. Basic Blue 3, CI. Basic Blue 5, CI. Acid Blue 15, CI. Mordant Blue 7.

Examples of the binder resin include polystyrene, a styrene-methacrylic acid copolymer, a styrene-methacylate copolymer, a styrene-acrylic acid copolymer, a styrene-acylate copolymer, a styrene-acrylonitrile copolymer, an acrylic resin, a styrene-maleic acid copolymer, polyvinyl chloride, polyvinyl acetate, an olefin resin, a polyester resin, a polyurethane resin and an epoxy resin. They may be used alone or in the form of a mixture thereof.

Examples of monomer(s) for preparing the binder resins include vinyl aromatic hydrocarbon monomers such as styrene, α-methylstyrene, vinyltoluene, chlorostyrene, ethylstyrene, and divinylbenzene; acrylic compound monomers such as acrylic acid, methacrylic acid, methyl acrylate, ethyl acrylate, butyl acrylate, 2-ethylhexyl acrylate, octyl acrylate, phenyl acrylate, methyl methacrylate, ethyl methacrylate, butyl methacrylate, 2-ethylhexyl methacrylate, octyl methacrylate, phenyl methacrylate; monocarboxylic acid derivatives having double bond such as acrylonitrile, methacrylonitrile and acrylamide; dicarboxylic acids and their derivatives such as maleic acid, methyl maleate, butyl maleate, dimethyl maleate, phthalic acid, succinic acid, and terephthalic acid; vinyl monomers such as ethylene, propylene, butylene, vinyl methyl ketone, vinyl hexyl ketone, vinyl methyl ether, and vinyl isobutyl ether; polyol compounds such as ethylene glycol, diethylene glycol, triethylene glycol, 1,2-propylene glycol, 1,3-propylene glycol, 1,4-butanediol, 1,6-hexanediol, bisphenol-A, hydrogenated bisphenol-A, and polyoxyethylenated bisphenol-A; isocyanates such as p-phenylene diisocyanate, p-xylylene diisocyanate, and 1,4-tetramethylene diisocyanate; amines such as ethylamine, butylamine, ethylenediamine, 1,4-dimaminobenzene, 1,4-diaminobutane, and monoethanolamine; and epoxy compounds such as diglycidyl ether, ethylene glycol diglycidyl ether, bisphenol-A glycidyl ether, and hydroquinone diglycidyl ether.

The electrophotographic toner of the present invention may be blended with optional additives, for example, fluidizers such as silicon oxide, anti-foggants such as mineral oils, various magnetic materials for one-component development, and conductive agents such as zinc oxide. The toner prepared in the present invention is mixed with, for example, an about 200-mesh iron powder (carrier) in a weight ratio of the toner to the iron powder of, for example, (3 to 8):(97 to 92) to prepare a developer for use in the step of development in the electrophotography.

Compared with toners wherein a conventional charge control agent is used, the electrophotographic toner of the present invention has a sharp distribution of charge and a good charge durability and therefore is characterized by a high capability of providing an image having a very high gradation and a very high capability of repeatedly forming an image.

BRIEF DESCRIPTION OF DRAWINGS

FIG. 2 shows an X-ray diffraction pattern of the compound used in Examples 15 and 8 (tetrabromobisphenol S) after the conversion to a form of fine particles.

In FIGS. 1 and 2, the abscissa represents an angle of diffraction ($2\theta$), while the ordinate represents the intensity of diffraction.

EXAMPLES

Figure 1:
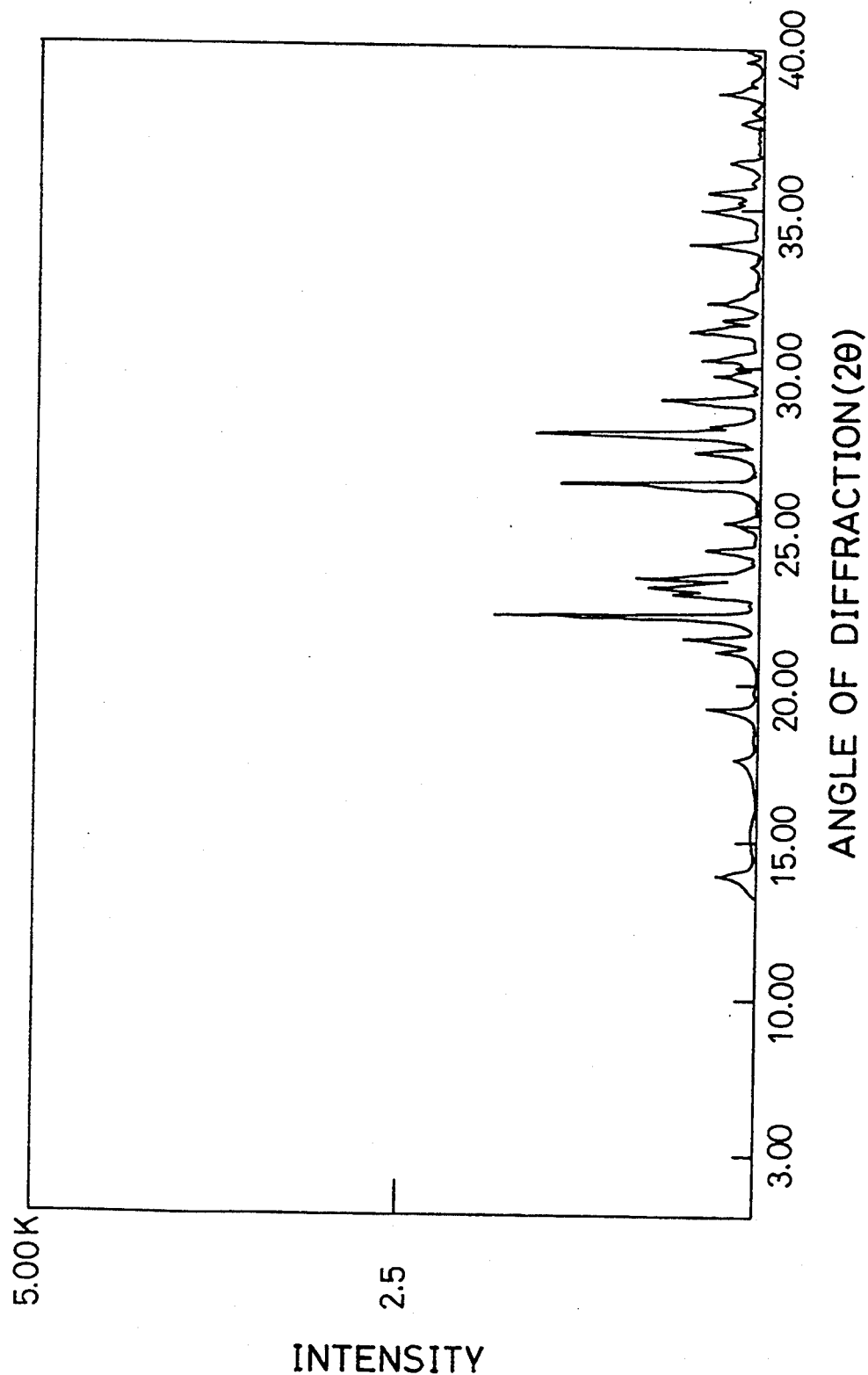
FIG. 1 shows an X-ray diffraction pattern of the compound used in Example 1 (tetrabromobisphenol S) before the conversion to a form of fine particles.

The present invention will now be described in more detail by referring to the following Examples, though it is not limited to these Examples only.

In the Examples, "parts" means "parts by weight" unless otherwise specified. The compound of the formula (1) wherein X is —$SO_2$— is referred to tetrabromobisphenol S, and that wherein X is —$C(CH_3)_2$— to tetrabromobisphenol A.

Example 1

| | |
|---|---|
| styrene-butyl acrylate copolymer (binder) | 100 parts |
| low molecular-weight polyethylene | 3 parts |
| CI. Disperse Yellow 164 (colorant) | 1.2 parts |

-continued

| | |
|---|---|
| tetrabromobisphenol S | 1.5 parts |

A mixture having the above-described composition was subjected to a melt mixing treatment (for 10 min) in a kneader adjusted to a temperature from 130° to 140° C. and then cooled for solidification. Then, the solid was coarsely crushed by means of a coarse crusher, pulverized by means of a jet mill pulverizer and classified by means of an air classifier to prepare a toner having a particle diameter of 5 to 20 μm.

The toner thus prepared was mixed with an about 200-mesh iron powder carrier in a weight ratio of the toner to the iron powder carrier of 3:97 to prepare developer A. The developer A was then subjected to measurement of an initial specific charge by means of a blow-off charge measurement apparatus and found to be −15.2 μC/g.

Next, the developer A was used for copying in a copying machine to give a clear yellow image having an excellent gradation without detrimental to the hue inherent in the colorant.

Further, the developer A was subjected to the charge stability test (a test for charge durability and a test for moisture resistance). The results are given in the following Table 1.

TABLE 1

| | Test for charge durability (specific chargeability, unit: −μC/g) | | | | | |
|---|---|---|---|---|---|---|
| Time (hr) | 0.25 | 0.5 | 1 | 2 | 4 | 6 |
| Developer A | 15.2 | 16.2 | 17.6 | 18.8 | 19.5 | 19.5 |

| Test for moisture resistance (specific chargeability, unit: −μC/g) | | |
|---|---|---|
| Initial | After test | Decrease (%) |
| 15.2 | 15.0 | 1.3 |

As is apparent from the above-described results, the developer A had a very excellent charge durability and good moisture resistance.

The test for charge stability was conducted by the following methods.

Test for change in charge durability:

A developer (a mixture of a toner with an iron powder carrier) A was weighed into a polyethylene vessel and subjected to ball milling at 120 rpm for 6 hr, thereby conducting contact chargeability. At that time, specific chargeabilities of the toner were measured at predetermined time intervals according to blow-off method.

Test for moisture resistance:

A developer was weighed into a polyethylene vessel in the same manner as that described above, and the polyethylene vessel was allowed to stand in an open state for two days in an atmosphere at a temperature of 35° C. and a humidity of 90% RH and subjected to ball milling at 120 rpm for 15 minutes to conduct contact chargeability. The specific chargeability of the toner was measured according to the blow-off method.

Example 2

| | |
|---|---|
| polyester resin (binder) | 100 parts |
| carbon black (colorant) | 6.0 parts |
| tetrabromobisphenol S | 1.5 parts |

A mixture having the above-described composition was subjected to a melt mixing treatment (for 10 min) in a kneader at a temperature adjusted to 150° to 180° C. and then cooled for solidification. The solid was coarsely crushed by means of a coarse crusher, pulverized by means of a jet mill pulverizer and classified by means of an air classifier to prepare a toner having a particle diameter of 5 to 20 μm.

The toner thus prepared was mixed with an about 200-mesh iron powder carrier in a weight ratio of the toner to the powder carrier in a weight ratio of the toner to the iron powder carrier of 3:97 to prepare developer B. The developer B was then subjected to measurement of an initial specific charge by means of a blow-off charge measurement apparatus and found to be −18.6 μC/g. Further, the developer B was used for copying in a copying machine to give a black image having an excellent gradation.

Further, the developer B was subjected to the charge stability test in the same manner as that of Example 1. The results are given in the following Table 2.

TABLE 2

| | Test for charge durability (specific chargeability, unit: −μC/g) | | | | | |
|---|---|---|---|---|---|---|
| Time (hr) | 0.25 | 0.5 | 1 | 2 | 4 | 6 |
| Developer B | 18.6 | 18.9 | 20.5 | 20.7 | 20.9 | 21.0 |

| Test for moisture resistance (specific chargeability, unit: −μC/g) | | |
|---|---|---|
| Initial | After test | Decrease (%) |
| 18.6 | 18.2 | 2.2 |

As is apparent from the above-described results, the developer B had a very excellent charge durability and good moisture resistance.

Example 3

| | |
|---|---|
| styrene-butyl acrylate copolymer (binder) | 100 parts |
| low-molecular-weight polypropylene | 3 parts |
| CI. Solvent Blue III (colorant) | 1.5 parts |
| tetrabromobisphenol S | 1.5 parts |

A mixture of these compounds was dissolved in 1000 parts of a solvent mixture of acetone and ethyl acetate, and the solution was stirred at room temperature for one hour. Then, the stirred mixture was added dropwise to 10000 parts of water while stirring for re-precipitation. The formed precipitates were collected by filtration and dried to prepare a toner in the coarse particle form. Subsequently, the toner was pulverized by means of a jet mill pulverizer and then classified by means of an air classifier to prepare a toner having a particle diameter of 5 to 20 μm.

The toner thus prepared was mixed with an about 200-mesh iron powder carrier in a weight ratio of the toner to the iron powder carrier of 3:97 to prepare developer C. The developer C was then subjected to measurement of an initial specific charge by means of a blow-off charge measurement apparatus and found to be −13.8 μC/g. Further, the developer C was used for copying in a copying machine to give a clear blue image having an excellent gradation without detriment to the hue inherent in the colorant.

Further, the developer C was subjected to the charge stability test in the same manner as that of Example 1. The results are given in the following Table 3.

TABLE 3

| | Test for charge durability (specific chargeability, unit: −µC/g) | | | | | |
|---|---|---|---|---|---|---|
| Time (hr) | 0.25 | 0.5 | 1 | 2 | 4 | 6 |
| Developer C | 13.8 | 14.3 | 16.9 | 17.5 | 19.2 | 19.2 |

| Test for moisture resistance (specific chargeability, unit: −µC/g) | | |
|---|---|---|
| Initial | After test | Decrease (%) |
| 13.8 | 13.4 | 2.9 |

As is apparent from the above-described results, the developer C had a very excellent charge durability and good moisture resistance.

Example 4

| | |
|---|---|
| epoxy resin (binder) | 100 parts |
| Cl. Disperse Red 60 (colorant) | 1.2 parts |
| Cl. Disperse Violet 17 (colorant) | 0.3 parts |
| tetrabromobisphenol S | 2.0 parts |

A mixture having the above-described composition was subjected to a melt mixing treatment in a kneader at a temperature adjusted to 130° to 150° C. and then spontaneously cooled for solidification. The solid was coarsely crushed by means of a coarse crusher, pulverized by means of a jet mill. pulverizer and further classified by means of an air classifier to prepare a toner having a particle diameter of 5 to 20 µm.

100 parts of the toner thus prepared was mixed with 0.3 part of a colloidal silica in a Henschel mixer. The mixture was then mixed with an about 200-mesh iron powder carrier in a weight ratio of the toner to the iron powder carrier of 3:97 to prepare developer D. The developer D was then subjected to measurement of an initial specific charge by means of a blow-off charge measurement apparatus and found to be −15.2 µC/g. Further, the developer D was used for copying in a copying machine to give a clear red image having an excellent gradation without detriment to the hue inherent in the colorant.

Further, the developer D was subjected to the charge stability test in the same manner as that of Example 1. The results are given in the following Table 4.

TABLE 4

| | Test for charge durability (specific chargeability, unit: −µC/g) | | | | | |
|---|---|---|---|---|---|---|
| Time (hr) | 0.25 | 0.5 | 1 | 2 | 4 | 6 |
| Developer D | 15.2 | 16.2 | 18.6 | 19.4 | 21.9 | 22.0 |

| Test for moisture resistance (specific chargeability, unit: −µC/g) | | |
|---|---|---|
| Initial | After test | Decrease (%) |
| 15.2 | 15.1 | 0.7 |

As is apparent form the above-described results, the developer D had a very excellent charge durability and good moisture resistance.

Example 5

| | |
|---|---|
| Styrene-butyl acrylate copolymer | 100 parts |
| Cl. Disperse Red 60 | 1.2 parts |
| tetrabromobisphenol A | 2.0 parts |

A mixture having the above-described composition was subjected to a melt mixing treatment in a kneader at a temperature adjusted to 130°–150° C. and then spontaneously cooled for solidification. The solid was coarsely crushed by means of a coarse crusher, pulverized by means of a jet mill pulverizer and further classified by means of an air classifier to prepare a toner having a particle diameter of 5 to 20 µm.

100 parts of the toner thus prepared was mixed with 0.3 part of a colloidal silica in a Henschel mixer. The mixture was then mixed with an about 200-mesh iron powder carrier in a weight ratio of the toner to the iron powder carrier of 3:97 to prepare developer E. The developer E was then subjected to measurement of an initial specific charge by means of a blow-off charge measurement apparatus and found to be +14.5 µC/g. Further, the developer E was used for copying in a copying machine to give a clear red image having an excellent gradation without detriment to the hue inherent in the colorant.

Further, the developer E was subjected to the charge stability test in the same manner as that of Example 1. The results are given in the following Table 5.

TABLE 5

| | Test for charge durability (specific chargeability, unit: +µC/g) | | | | | |
|---|---|---|---|---|---|---|
| Time (hr) | 0.25 | 0.5 | 1 | 2 | 4 | 6 |
| Developer E | 14.5 | 15.0 | 16.5 | 15.2 | 15.8 | 14.9 |

| Test for moisture resistance (specific chargeability, unit: +µC/g) | | |
|---|---|---|
| Initial | After test | Decrease (%) |
| 14.5 | 14.1 | 2.8 |

As is apparent from the above-described results, the developer E had a very excellent charge durability and good moisture resistance.

Example 6

| | |
|---|---|
| styrene-butyl acrylate copolymer (binder) | 100 parts |
| low-molecular-weight polyethylene | 3 parts |
| Kayaset Yellow 963 (colorant) (Styryl dye: a product of Nippon Kayaku Co., Ltd.) | 1.2 parts |
| tetrabromobisphenol A | 1.5 parts |

A mixture having the above-described composition was subjected to a melt mixing treatment (for 10 min) in a kneader at a temperature adjusted to 125°–140° C. and then cooled for solidification. The solid was coarsely crushed by means of a coarse crusher, pulverized by means of a jet mill pulverizer and classified by means of an air classifier to prepare a toner having a particle diameter of 5 to 20 µm.

The toner thus prepared was mixed with an about 200-mesh iron powder carrier in a weight ratio of the toner to the iron powder carrier of 3:97 to prepare developer F. The developer F was then subjected to measurement of an initial specific charge by means of a blow-off charge measurement apparatus and found to be +15.0 µC/g. Further, the developer F was used for copying in a copying machine to give a clear yellow image having an excellent gradation without detriment to the hue inherent in the colorant.

Further, the developer F was subjected to the charge stability test in the same manner as that of Example 1. The results are given in the following Table 6.

TABLE 6

Test for charge durability

TABLE 6-continued

| | (specific chargeability, unit: +μC/g) | | | | | |
|---|---|---|---|---|---|---|
| Time (hr) | 0.25 | 0.5 | 1 | 2 | 4 | 6 |
| Developer F | 15.0 | 15.5 | 17.0 | 16.1 | 15.8 | 15.6 |

| Test for moisture resistance (specific chargeability, unit: +μC/g) | | |
|---|---|---|
| Initial | After test | Decrease (%) |
| 15.0 | 14.9 | 0.7 |

As is apparent from the above-described results, the developer F had a very excellent charge durability and good moisture resistance.

Example 7

| | |
|---|---|
| methylstyrene monomer | 75 parts |
| ethyl acrylate monomer | 20 parts |
| Kayaset Blue 814 (colorant) | 1.8 parts |
| (Anthraquinone dye: a product of Nippon Kayaku Co., Ltd.) | |
| benzoyl peroxide | 6 parts |
| tetrabromobisphenol S | 2 parts |

A mixture having the above-described composition was mixed for 5 minutes using a homo-mixer to form a homogeneous liquid. The liquid was added to a dispersion of 2.3 parts of magnesium carbonate in 120 parts of water, followed by mixing in a homo-mixer at 6500 rpm for 5 minutes to obtain a homogeneous suspension. The suspension was then placed in a 300 ml three-necked flask and the polymerization was carried out at 70° C. for 5 hr under stirring at 200 rpm. After the mixture was cooled to 40° C., 90 parts of 5% diluted hydrochloric acid was added thereto. The resulting precipitates were collected by filtration, washed with water, and dried at 40° C. to obtain a toner having a particle diameter of 5 to 20 μm.

100 parts of the toner thus prepared was mixed with 0.3 part of a colloidal silica in a Henschel mixer. The mixture was then mixed with an about 200-mesh iron powder carrier in a weight ratio of the toner to the iron powder carrier of 3:97 to prepare developer G. The developer G was then subjected to measurement of an initial specific charge by means of a blow-off charge measurement apparatus and found to be −15.7 μC/g. Further, the developer G was used for copying in a copying machine to give a clear red image having an excellent gradation without detriment to the hue inherent in the colorant.

Further, the developer G was subjected to the charge stability test in the same manner as that of Example 1. The results are given in the following Table 7.

TABLE 7

| | Test for charge durability (specific chargeability, unit: −μC/g) | | | | | |
|---|---|---|---|---|---|---|
| Time (hr) | 0.25 | 0.5 | 1 | 2 | 4 | 6 |
| Developer G | 15.7 | 16.2 | 17.1 | 17.2 | 17.8 | 17.9 |

| Test for moisture resistance (specific chargeability, unit: −μC/g) | | |
|---|---|---|
| Initial | After test | Decrease (%) |
| 15.7 | 15.5 | 1.3 |

As is apparent from the above-described results, the developer G had a very excellent charge durability and good moisture resistance.

Examples 8

An alkaline aqueous solution was prepared by adding 9.6 parts of sodium hydroxide to 200 parts of water. 50 parts of tetrabromobisphenol S having a diameter of 10–15 μm was added thereto and completely dissolved. An acidic solution prepared by diluting 15 parts of conc. sulfuric acid using 200 parts of water was added dropwise thereto under stirring over a period of 30 minutes to 1 hour, while maintaining the temperature of the solution at 20°–30° C. After adding the acidic aqueous solution and confirming the resulting solution to be weakly acidic upon 30 minutes stirring, the precipitated crystals were filtered off, washed with 300 parts of water, and dried to obtain 49.5 parts of charge control agent of the invention consisting of tetrabromobisphenol S which was in a form of fine particles (mp=290°–291° C.). The particles were verified to be uniform ones having a diameter of 1 to 3 μm by analysis using electron microscope. The X-ray diffraction pattern is shown in FIG. 2.

The X-ray diffraction pattern was measured according to X-ray powder diffractometry and recorded the diffraction by Cu—Kα line using a proportional counter.

Example 9

In Example 8, the order of the addition was reversed. That is, the alkaline aqueous solution of tetrabromobisphenol S was added to the aqueous solution of sulfuric acid to precipitate the crystals. From electronic microscopic analysis of the crystals, it was verified that the crystals thus obtained were also in a form of uniform fine particles having a diameter of 1–3 μm as in Example 8.

Examples 10 and 11

Crystals were precipitated in a similar manner to Example 8 except that sulfuric acid was replaced to hydrochloric acid (Example 10) or acetic acid (Example 11). From electron microscopic analysis of the crystals, it was verified that the crystals thus obtained were also in a form of uniform fine particles having a diameter of 1–3 μm as in Example 8.

Examples 12

An alkaline aqueous solution was prepared by adding 17.2 parts of sodium carbonate to 250 parts of water. 45 parts of tetrabromobisphenol S was added thereto and completely dissolved. An acidic solution prepared by diluting 10 parts of conc. sulfuric acid using 100 parts of water was added dropwise thereto under stirring over a period of 30 minutes to 1 hour, while maintaining the temperature of the solution at 20°–30° C. After adding the acidic aqueous solution and confirming the resulting solution to be weakly acidic upon 30 minutes stirring, the precipitated crystals were filtered off, washed with 300 parts of water, and dried to obtain 49.3 parts of charge control agent of the invention consisting of tetrabromobisphenol S. The particles were verified to be uniform ones having a diameter of 1 to 3 μm by analysis using electron microscope.

Example 13

Crystals were precipitated in a similar manner to Example 12 except that sodium carbonate was replaced to potassium hydroxide. Electron microscopic analysis of the crystals verified that the crystals thus obtained were also in a form of uniform fine particles having a diameter of 1–3 μm as in Example 8.

Examples 14

An alkaline aqueous solution was prepared by adding 6.4 parts of sodium hydroxide to 250 parts of water. 42.0 parts of tetrabromobisphenol A was added thereto and completely dissolved. An acidic solution prepared by diluting 10 parts of conc. sulfuric acid with 100 parts of water was added dropwise thereto under stirring while maintaining a temperature of the solution to be 20°–30° C. over a period of 30 minutes to 1 hour. After adding the acidic aqueous solution and confirming the resulting solution to be weakly acidic upon 30 minutes stirring, the precipitated crystals were filtered off, washed with 300 parts of water, and dried to obtain 41.5 parts of charge control agent of the invention consisting of tetrabromobisphenol A. The particles were verified to be uniform ones having a diameter of 2 to 4 μm by analysis using electron microscope.

Example 15

| styrene-butyl acrylate copolymer (binder) | 100 parts |
| low molecular-weight polyethylene | 3 parts |
| CI. Disperse Yellow 164 (colorant) | 1.2 parts |
| the charge control agent obtained in Example 8 | 1.5 parts |

A mixture having the above-described composition was subjected to a melt mixing treatment (for 10 min) in a kneader adjusted to a temperature from 130° to 140° C. and then cooled for solidification. The solid was coarsely crushed by means of a coarse crusher, pulverized by means of a jet mill pulverizer and classified by means of an air classifier to prepare a toner of the invention having a particle diameter of 5 to 20 μm. The dispersibility at melt mixing treatment was observed to be extremely good upon microscopic analysis.

The toner thus prepared was mixed with an about 200-mesh iron powder carrier in a weight ratio of the toner to the iron powder carrier of 3:97 to prepare developer H. The developer H was then subjected to measurement of an initial specific charge by means of a blow-off charge measurement apparatus and found to be −15.7 μC/g.

Next, the developer H was used for copying in a copying machine to give a clear yellow image having an excellent gradation without detrimental to the hue inherent in the colorant.

Further, the developer H was subjected to the charge stability test. The results are given in the following Table 8.

TABLE 8

| | Test for charge durability (specific chargeability, unit: −μC/g) | | | | | |
|---|---|---|---|---|---|---|
| Time (hr) | 0.25 | 0.5 | 1 | 2 | 4 | 6 |
| Developer H | 15.7 | 16.6 | 18.1 | 18.4 | 19.9 | 20.1 |

| Test for moisture resistance (specific chargeability, unit: −μC/g) | | |
|---|---|---|
| Initial | After test | Decrease (%) |
| 15.7 | 15.5 | 1.3 |

As is apparent from the above-described results, the developer H had a very excellent charge durability and good moisture resistance.

Example 16

| styrene-butyl acrylate copolymer (binder) | 100 parts |
| low molecular-weight polyethylene | 3 parts |
| CI. Disperse Yellow 164 (colorant) | 1.2 parts |
| the charge control agent obtained in Example 14 | 1.5 parts |

A mixture having the above-described composition was subjected to a melt mixing treatment (for 10 min) in a kneader adjusted to a temperature from 130° to 140° C. and then cooled for solidification. The solid was coarsely crushed by means of a coarse crusher, pulverized by means of a jet mill pulverizer and classified by means of an air classifier to prepare a toner of the invention having a particle diameter of 5 to 20 μm. The dispersibility at melt mixing treatment was observed to be extremely good upon microscopic analysis as in Example 15.

The toner thus prepared was mixed with an about 200-mesh iron powder carrier in a weight ratio of the toner to the iron powder carrier of 3:97 to prepare developer I. The developer I was then subjected to measurement of an initial specific charge by means of a blow-off charge measurement apparatus and found to be +16.0 μC/g.

Next, the developer I was used for copying in a copying machine to give a clear yellow image having an excellent gradation without detrimental to the hue inherent in the colorant.

Further, the developer I was subjected to the charge stability test. The results are given in the following Table 9.

TABLE 9

| | Test for charge durability (specific chargeability, unit: +μC/g) | | | | | |
|---|---|---|---|---|---|---|
| Time (hr) | 0.25 | 0.5 | 1 | 2 | 4 | 6 |
| Developer I | 16.0 | 16.5 | 17.0 | 16.1 | 16.8 | 16.6 |

| Test for moisture resistance (specific chargeability, unit: +μC/g) | | |
|---|---|---|
| Initial | After test | Decrease (%) |
| 16.0 | 15.9 | 0.6 |

As is apparent from the above-described results, the developer I had a very excellent charge durability and good moisture resistance.

Comparative Example 1

A developer toner was prepared in a similar manner to Example 1 except that tetrabromobisphenol S was replaced to the compound of the following formula (2). The toner thus prepared was mixed with an about 200-mesh iron powder carrier in a weight ratio of the toner to the iron powder carrier of 3:97 to prepare developer J. The developer J was then subjected to measurement of an initial specific charge by means of a blow-off charge measurement apparatus and found to be −6.1 μC/g which is insufficient for actual use. Further, the developer J was used for copying in a copying machine to result in a decrease of image density as the copying proceeds.

Further, the developer J was subjected to the charge stability test in the same manner as that of Example 1. The results are given in the following Table 10.

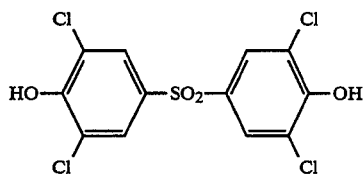

(2)

TABLE 10

| | Test for charge durability (specific chargeability, unit: $-\mu C/g$) | | | | | |
|---|---|---|---|---|---|---|
| Time (hr) | 0.25 | 0.5 | 1 | 2 | 4 | 6 |
| Developer J | 6.1 | 7.3 | 9.6 | 11.3 | 13.5 | 14.1 |

| Test for moisture resistance (specific chargeability, unit: $-\mu C/g$) | | |
|---|---|---|
| Initial | After test | Decrease (%) |
| 6.1 | 5.0 | 18.0 |

As is apparent from the above-described results, the developer J had a poor charge durability and poor moisture resistance.

Comparative Example 2

A developer toner was prepared in a similar manner to Example 2 except that tetrabromobisphenol S was replaced to the compound of the following formula (3). The toner thus prepared was mixed with an about 200-mesh iron powder carrier in a weight ratio of the toner to the iron powder carrier of 3:97 to prepare developer K. The developer K was then subjected to measurement of an initial specific charge by means of a blow-off charge measurement apparatus and found to be $-9.3$ $\mu C/g$ which is insufficient for actual use. Further, the developer K was used for copying in a copying machine to result in a decrease of image density as the copying proceeds.

Further, the developer K was subjected to the charge stability test in the same manner as that of Example 2. The results are given in the following Table 11.

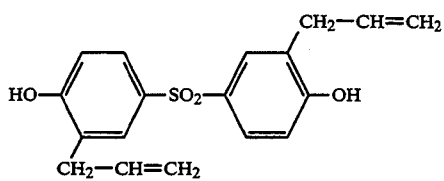

(3)

TABLE 11

Test for charge durability

TABLE 11-continued

| (specific chargeability, unit: $-\mu C/g$) | | | | | |
|---|---|---|---|---|---|
| Time (hr) | 0.25 | 0.5 | 1 | 2 | 4 | 6 |
| Developer K | 9.3 | 10.5 | 12.1 | 13.4 | 14.4 | 14.4 |

| Test for moisture resistance (specific chargeability, unit: $-\mu C/g$) | | |
|---|---|---|
| Initial | After test | Decrease (%) |
| 9.3 | 8.1 | 12.9 |

As is apparent from the above-described results, the developer K had a poor charge durability and poor moisture resistance.

It is evident from the above comparative tests that the present toners comprising the compound of the formula (1) were superior to the conventional toners in that they had, in combination, the characteristics of greater specific chargeability, better charge durability and better moisture resistance.

What is claimed is:

1. An electrophotographic toner containing particles of the compound represented by the following formula (1) as a charge control agent:

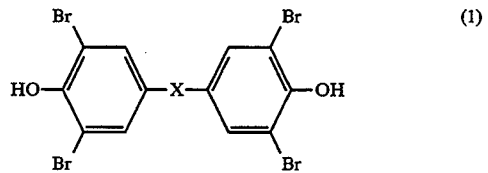

(1)

wherein X represents $SO_2$, said particles having a diameter less than 5 $\mu$m.

2. A process for producing a compound of the formula (1) for an electrophotographic toner according to claim 1, comprising dissolving the compound represented by the formula (1) into an alkaline solution and treating the resulting solution with an acid to precipitate particles of said compound having a diameter less than 5 $\mu$m.

3. An electrophotographic toner comprising 99 to 65% by weight of a binder resin, 1.0 to 15% by weight of a colorant, and 0.1 to 30% by weight of the compound represented by the above formula (1).

4. An electrophotographic toner according to claim 3, comprising 98 to 85% by weight of a binder resin, 1.5 to 10% by weight of a colorant, and 0.5 to 5% by weight of the compound represented by the formula (1).

5. An electrophotographic toner according to claim 1, 3 or 4, wherein the said compound of formula (1) has a diameter of 1 to 3$\mu$.

6. A process according to claim 2, wherein said compound has a diameter of 1 to 3 $\mu$m.

* * * * *